(12) United States Patent
Posada

(10) Patent No.: US 8,383,674 B1
(45) Date of Patent: Feb. 26, 2013

(54) SYNTHESIS OF SILVER NANOCLUSTERS ON ZEOLITE SUBSTRATES

(75) Inventor: Yury Posada, San Juan, PR (US)

(73) Assignee: University of Puerto Rico, San Juan, PR (US)

( * ) Notice: Subject to any disclaimer, the term of this patent is extended or adjusted under 35 U.S.C. 154(b) by 231 days.

(21) Appl. No.: 12/803,745

(22) Filed: Jul. 1, 2010

Related U.S. Application Data

(60) Provisional application No. 61/222,330, filed on Jul. 1, 2009.

(51) Int. Cl.
*A61K 31/28* (2006.01)
*A61K 33/38* (2006.01)
(52) U.S. Cl. ......... 514/495; 514/492; 424/617; 424/618
(58) Field of Classification Search .................. 514/492, 514/495; 424/617, 618
See application file for complete search history.

(56) References Cited

U.S. PATENT DOCUMENTS

2010/0276630 A1* 11/2010 Chandrasekhar et al. ...... 252/74

OTHER PUBLICATIONS

Skrabalak et al. "On the Polyol Synthesis of Silver Nanostructures: Glycolaldehyde as a Reducing Agent," Nano Letters, 2008, 8(7), pp. 2077-2081.*
Y. Posada, "Synthesis of silver nanoclusters on zeolite substrates," J. Appl. Phys. 2009, 105, pp. 126108-1-126108-3.*

* cited by examiner

*Primary Examiner* — James H. Alstrum-Acevedo
(74) *Attorney, Agent, or Firm* — Hoglund & Pamias, P.S.C.; Roberto J. Rios

(57) ABSTRACT

Silver nanoclusters were synthesized by reducing silver nitrate with ethylene glycol at a certain temperature in the presence of zeolite. A one-pot procedure rendered uniform size distributions of quasi-spherical silver clusters synthesized on the surfaces of cubic-like zeolite.

6 Claims, 3 Drawing Sheets

SYNTHESIS OF SILVER NANOCLUSTERS ON ZEOLITE SUBSTRATES

FIELD OF THE INVENTION

The present invention relates to the synthesis of silver nanoclusters, and more specifically to the synthesis of silver nanoclusters on the presence of zeolite.

BACKGROUND OF THE INVENTION

Zeolites are very attractive host materials for developing nanocomposites due to their ability to selectively exchange and integrate transition metals, salts, charged and neutral species within their cages and interconnecting channels. Ion exchange research studies in zeolites started in the 1950s' when the formation of superlattices in these systems was reported. Since then, many research advances have been accomplished in the development and study of the properties of various metal ions in zeolite frameworks. Currently, silver zeolite materials have many applications in different areas such as catalysis, biological labeling, medicine, water treatment, antibacterial products, optoelectronics, and surface enhanced Raman scattering.

Aqueous ion exchange and molten salts have been the regular methods to introduce cationic species inside the cages of various types of zeolites. In addition, the physical and chemical properties of the host materials produced by those techniques have been controlled and improved by annealing under inert and reactive atmospheres. Manufacture of high quality silver zeolite implies long reactions times, usually over 20 hours, and a highly trained production workforce along with special facilities to handle high temperatures and very-low- vacuum systems. In order to overcome this technical scenario, a variant of the so-called "polyol" process is applied in which silver nitrate is reduced by ethylene glycol in the presence of a polymer cationic binder. The polyol method has proven to control shape, purity, and size distribution of metallic silver nanostructures. However, what is needed is a simple, cost-effective synthesis method for the production of silver nanoclusters.

SUMMARY OF THE INVENTION

The synthetic procedure of the present invention is carried out in the presence of a zeolite producing silver nanoclusters zeolite According to an aspect of the invention, a mixture of ethylene glycol and zeolite is prepared; and silver nitrate is then added to said mixture.

According to one aspect of the invention, ethylene oxide could alternatively be mixed with the zeolite.

According to another aspect of the invention, the mixture of ethylene oxide and zeolite is stirred and heated until it reaches 160° C. In accordance to another aspect of the invention, the zeolite comprises sodium aluminosilicate, zeolite powder.

In still another aspect of the invention, silver nitrate is added to said mixture at a molar proportion of about 0.6-1:2 of silver nitrate to zeolite.

BRIEF DESCRIPTION OF THE DRAWINGS

Further features and advantages of the invention will become apparent from the following detailed description taken in conjunction with the accompanying figures showing illustrative embodiments of the invention, in which.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

Silver nanoclusters were prepared by reducing silver nitrate (ACS grade) with ethylene glycol (reagent plus 99% pure) in the presence of NaA-zeolite powder ($Na_2[Al_2SiO_6]$ ·nH2O; 99.9%). Other equivalent zeolite structures could be used to produce the same phenomena. Silver nitrate was added to a mixture of ethylene glycol and zeolite that were previously stirred and heated at 160° C. for about 30 minutes or until the desired temperature is reached. A molar proportion of 0.6-1:2 of silver nitrate to zeolite produced immediately a light silvery gray material. The temperature during the reaction was kept at about 160° C. The mixture was then allowed to react for about 15 minutes to assure the reaction was completed and finally was allowed to cool at room temperature. The precipitate was filtered and washed several times with dionized water. Physical and chemical characterizations were determined with a JEOL 5800LV scanning electron microscope (SEM) with low vacuum, and with X-ray fluorescence (EDAX); surface analysis was achieved with a PHI 5600ci X-ray photoelectron (XPS or ESCA).

Figure 1:
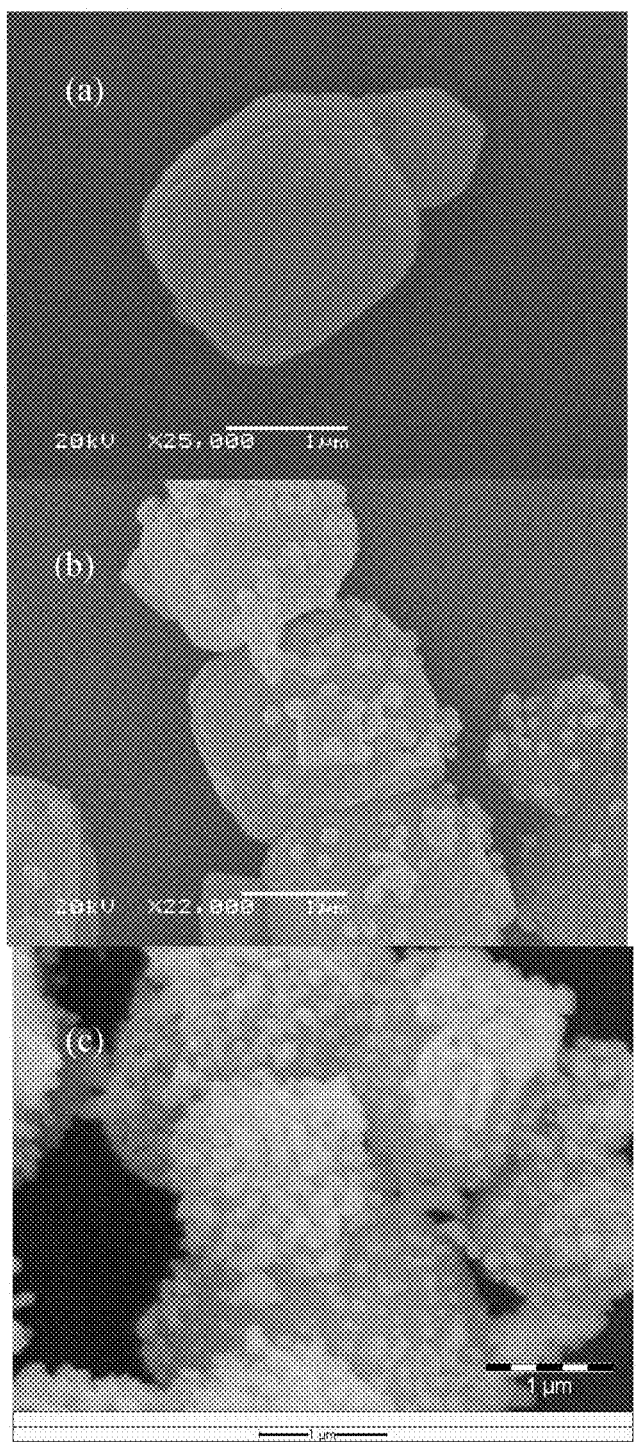
FIG. 1 shows comparative SEM images of untreated smooth zeolite substrates, and Agn-Z samples showing silver nanoclusters according to the present invention.

The Agn-Z samples analyzed were prepared using the above-mentioned molar proportion since it was found that the material's color did not darken with increased reaction time. Morphological analysis of bulk materials shows in FIG. 1, a SEM image (a) of untreated smooth zeolite substrates, a SEM image (b) of an Agn-Z sample of –1 μm with silver nanoclusters of 100 to 200 nm, and a SEM image (c) of an Agn-Z sample with high concentration of silver nanoclusters. EDAX microanalysis of sample (c) showed a maximum concentration of 38 wt % of silver.

Figure 2:
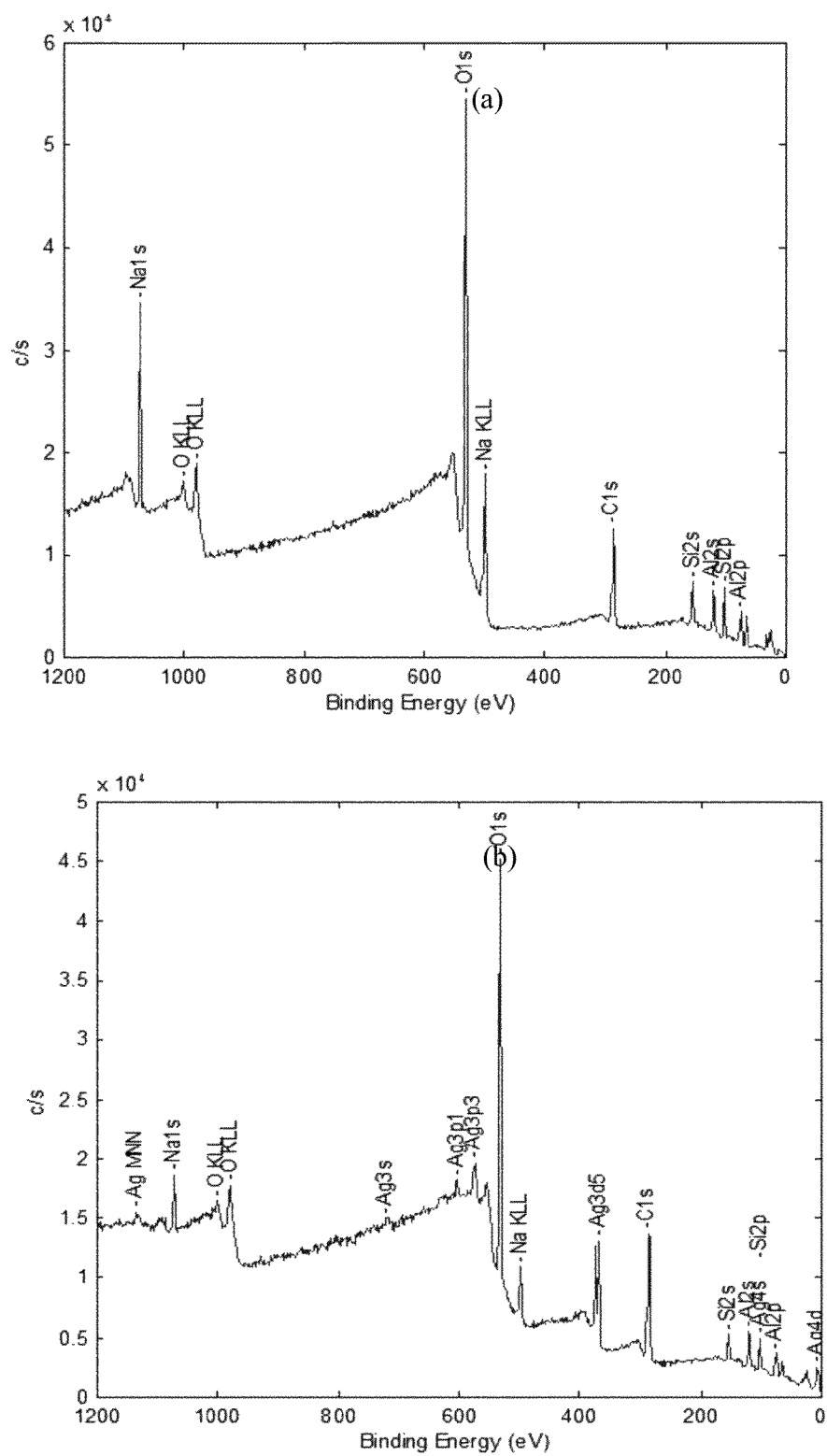
FIG. 2 shows XPS spectra for untreated zeolite, and Agn-Z sample according to the present invention.
Figure 3:
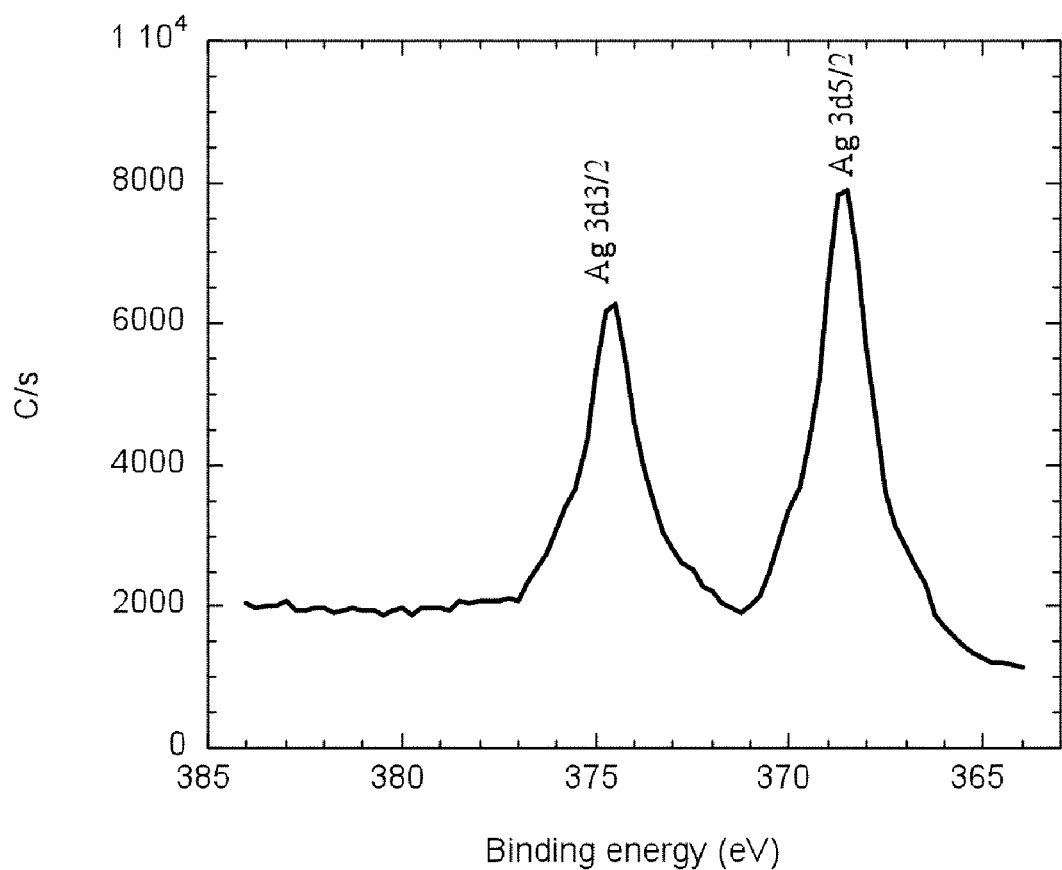
FIG. 3 shows XPS spectra for the Ag $3d_{5/2}$ core electrons according to the present invention.

FIG. 2 shows the results of surface analysis, wherein plot (a) illustrates XPS full spectra for an untreated zeolite, and plot (b) illustrates XPS full spectra for an Agn-Z sample with high concentration of silver nanoclusters. Silver atomic concentrations ranged from 3.1 to 5.7%. No traces of nitrogen were measured which could indicate that the silver signal corresponds mostly to silver species. FIG. 3 is a plot showing the spectra for the $Ag3d_{5/2}$ core electrons with binding energy at 368.6 eV, which is higher than the binding energy of metallic silver (368.3 eV); this shifting could be attributed to size effects.

Gold-Silver Nanoclusters on Zeolite Substrates

Silver nanoclusters that were synthesized using the technique described herein were fuctionalized with gold nanoparticles by adding drops of a solution 1.0 M of $HAuCl_4$ to a suspension of silver nanoclusters on zeolites at 160° C. The silvery gray suspension changed its color to a bluish color immediately after adding the $HAuCl_4$, indicating the formation of gold nanoparticles that were attracted onto the silver nanoclusters. Silver nanoclusters have potential to enhance Raman scattering for sensing and biodetection applications and the gold nanoparticles could be used as conductive composites and for photo-triggered drug delivery. Gold-silver nanocornposites could serve as building blocks to construct more complex macromolecules and lattices.

Silver Nanoclusters on Zeolite Substrates Films for Photovoltaic Cells

Annealing at 300° C. silver nanoclusters on zeolite substrates prepared by the technique described herein produces blue-green photoluminescence under excitation with UV light. This phenomenon could be used to improve solar cells efficiency and have a great potential for developing photovoltaic cells.

Silver Nanoclusters on Zeolite Substrates for Antibacterial, Antifungal and Antivirus Applications Silver natural antibacterial, antifungal and antivirus properties have great potential for applications in the health industry. Silver nanoclusters on zeolite substrate could make into air filters for operation rooms at hospital facilities, also a can be used to clean thoroughly surgical areas and equipment to create emergency aseptic environments.

It is proposed that the technique of the present invention could potentially be applied to other transition metals and could be optimized to obtain silver nanodots or other structures.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

I claim:

1. A method of synthesizing silver nanomaterials comprising: preparing a mixture of ethylene glycol and zeolite, and adding silver nitrate to said mixture, wherein preparing the mixture of ethylene glycol and zeolite comprises stirring said mixture until it reaches a first temperature of about 160° C.

2. The method of claim 1, wherein said zeolite comprises sodium aluminosilicate, zeolite.

3. The method of claim 1, wherein silver nitrate is added to said mixture at a molar proportion of about 0.6-1:2 of silver nitrate to zeolite.

4. The method of claim 1, further comprising allowing the reaction to cool at room temperature.

5. The method of claim 4, further comprising filtering and washing a resulting precipitate.

6. The method of claim 1, wherein said zeolite comprises zeolite powder.

* * * * *